US010156324B2

(12) United States Patent
Ito

(10) Patent No.: US 10,156,324 B2
(45) Date of Patent: Dec. 18, 2018

(54) LIGHT SOURCE DEVICE AND ENDOSCOPE APPARATUS COMPRISING THE SAME

(71) Applicant: OLYMPUS CORPORATION, Tokyo (JP)

(72) Inventor: Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 143 days.

(21) Appl. No.: 15/393,024

(22) Filed: Dec. 28, 2016

(65) Prior Publication Data

US 2017/0108183 A1 Apr. 20, 2017

Related U.S. Application Data

(63) Continuation of application No. 15/051,104, filed on Feb. 23, 2016, now Pat. No. 9,587,791, which is a (Continued)

(30) Foreign Application Priority Data

Dec. 26, 2007 (JP) ................................ 2007-335321

(51) Int. Cl.
*A61B 1/06* (2006.01)
*F21K 9/64* (2016.01)
(Continued)

(52) U.S. Cl.
CPC ................ *F21K 9/64* (2016.08); *A61B 1/063* (2013.01); *A61B 1/0638* (2013.01); (Continued)

(58) Field of Classification Search
None
See application file for complete search history.

(56) References Cited

U.S. PATENT DOCUMENTS 7,020,378 B2 3/2006 Poisel et al.
2002/0070681 A1 6/2002 Shimizu et al.
(Continued)

FOREIGN PATENT DOCUMENTS

EP 1 575 423 A1 9/2005
EP 1 672 754 A2 6/2006
(Continued)

OTHER PUBLICATIONS

Japanese Official Action dated Jan. 10, 2017 from corresponding Japanese Patent Application No. 2016-029099 together with English language translation.

(Continued)

*Primary Examiner* — Andrew Coughlin
(74) *Attorney, Agent, or Firm* — Scully, Scott, Murphy & Presser, P.C.

(57) ABSTRACT

A light source device includes a first semiconductor light source, a second semiconductor light source, and a wavelength converter. The first semiconductor light source emits light in a first wavelength range. The second semiconductor light source emits light in a second wavelength range different from the first wavelength range. The wavelength converter absorbs the light in the first wavelength range to emit light in a third wavelength range different from either of the first wavelength range and the second wavelength range, and transmits the light in the second wavelength range substantially entirely.

23 Claims, 9 Drawing Sheets

Related U.S. Application Data continuation of application No. 14/293,551, filed on Jun. 2, 2014, now Pat. No. 9,303,830, which is a continuation of application No. 13/909,554, filed on Jun. 4, 2013, now Pat. No. 8,810,126, which is a continuation of application No. 12/335,833, filed on Dec. 16, 2008, now Pat. No. 8,698,387.

(51) Int. Cl.

| | |
|---|---|
| ***F21V 8/00*** | (2006.01) |
| ***G02B 23/24*** | (2006.01) |
| ***F21V 9/30*** | (2018.01) |
| ***A61B 1/07*** | (2006.01) |
| *H01S 5/40* | (2006.01) |
| *F21Y 115/30* | (2016.01) |

(52) U.S. Cl.

CPC .......... *A61B 1/0653* (2013.01); *A61B 1/0661* (2013.01); *A61B 1/0676* (2013.01); *A61B 1/07* (2013.01); *F21V 9/30* (2018.02); *G02B 6/001* (2013.01); *G02B 6/0003* (2013.01); *G02B 6/0006* (2013.01); *G02B 6/0008* (2013.01); *G02B 23/2469* (2013.01); *H01S 5/4087* (2013.01); *F21Y 2115/30* (2016.08); *H01S 5/4025* (2013.01)

(56) References Cited

U.S. PATENT DOCUMENTS

| | | | |
|---|---|---|---|
| 2003/0007087 | A1 | 1/2003 | Hakamata et al. |
| 2003/0042493 | A1 | 3/2003 | Kazakevich |
| 2003/0143510 | A1 | 7/2003 | Berube-Lauziere et al. |
| 2003/0176768 | A1 | 9/2003 | Gono et al. |
| 2004/0207313 | A1 | 10/2004 | Omoto et al. |
| 2004/0217692 | A1 | 11/2004 | Cho et al. |
| 2005/0006659 | A1 | 1/2005 | Ng et al. |
| 2005/0012986 | A1 | 1/2005 | Kakui |
| 2005/0182321 | A1 | 8/2005 | Frangioni |
| 2006/0028122 | A1 | 2/2006 | Wang et al. |
| 2006/0043879 | A1 | 3/2006 | Naitou |
| 2006/0152926 | A1 | 7/2006 | Hama et al. |
| 2006/0235277 | A1 | 10/2006 | Ohkubo et al. |
| 2006/0287582 | A1 | 12/2006 | Toda |
| 2007/0153512 | A1 | 7/2007 | Hendrie |
| 2007/0159064 | A1 | 7/2007 | Choi |
| 2007/0297190 | A1 | 12/2007 | Ng |
| 2008/0112182 | A1 | 5/2008 | Kazakevich |
| 2008/0130311 | A1 | 6/2008 | Kazakevich |
| 2008/0192458 | A1 | 8/2008 | Li |
| 2008/0205477 | A1 | 8/2008 | Hama et al. |
| 2008/0262316 | A1 | 10/2008 | Ajima et al. |
| 2009/0040781 | A1 | 2/2009 | Ito |
| 2011/0034770 | A1 | 2/2011 | Endo et al. |
| 2011/0165534 | A1 | 7/2011 | Berube-Lauziere |
| 2011/0205751 | A1 | 8/2011 | Kazakevich |
| 2014/0029290 | A1 | 1/2014 | Kazakevich |
| 2014/0084323 | A1 | 3/2014 | Shimizu et al. |
| 2014/0268643 | A1 | 9/2014 | Ito |

FOREIGN PATENT DOCUMENTS

| | | | |
|---|---|---|---|
| EP | 1 795 798 | A1 | 6/2007 |
| EP | 2 026 108 | A1 | 2/2009 |
| JP | H07-155291 | A | 6/1995 |
| JP | H-10-216085 | A | 8/1998 |
| JP | 2000-208815 | A | 7/2000 |
| JP | 2001-170009 | A | 6/2001 |
| JP | 2002-034908 | A | 2/2002 |
| JP | 2003-019112 | A | 1/2003 |
| JP | 2003-153852 | A | 5/2003 |
| JP | 2003-520635 | A | 7/2003 |
| JP | 2003-526035 | A | 9/2003 |
| JP | 2005-502083 | A | 1/2005 |
| JP | 2005-033211 | A | 2/2005 |
| JP | 2005-39126 | A | 2/2005 |
| JP | 2005-198794 | A | 7/2005 |
| JP | 2005-294288 | A | 10/2005 |
| JP | 2006-020883 | A | 1/2006 |
| JP | 2006-026128 | A | 2/2006 |
| JP | 2006-061685 | A | 3/2006 |
| JP | 2006-167305 | A | 6/2006 |
| JP | 2006-173324 | A | 6/2006 |
| JP | 2006-296656 | A | 11/2006 |
| JP | 2006-314686 | A | 11/2006 |
| JP | 2006-526428 | A | 11/2006 |
| JP | 2006-346185 | A | 12/2006 |
| JP | 2007-123946 | A | 5/2007 |
| JP | 2007-258019 | A | 10/2007 |
| JP | 2007-315942 | A | 12/2007 |
| JP | 2009-153712 | A | 7/2009 |
| JP | 2011-36361 | A | 2/2011 |
| JP | 2013-116379 | A | 6/2013 |
| JP | 2013-128785 | | 7/2013 |
| JP | 2013-128786 | A | 7/2013 |
| JP | 2013-135933 | | 7/2013 |
| JP | 2013-154185 | | 8/2013 |
| WO | 99/22127 | A1 | 5/1999 |

OTHER PUBLICATIONS

Japanese Office Action dated Jun. 24, 2014 in counterpart Japanese Patent Application No. 2013-055467, together with an English language translation.

Japanese Office Action dated Jun. 24, 2014 in counterpart Japanese Patent Application No. 2013-055465, together with an English language translation.

Japanese Office Action dated Jun. 24, 2014 in counterpart Japanese Patent Application No. 2013-055466, together with an English language translation.

Japanese Office Action dated Jun. 24, 2014 in counterpart Japanese Patent Application No. 2013-055464, together with an English language translation.

Japanese Office Action dated Jun. 24, 2014 in counterpart Japanese Patent Application No. 2013-055463, together with an English language translation.

Kato, Masayuki, et al., "New Imaging Diagnosis of Digestive Tract and Adoption of EMR in Applied Stomach Upheaval-type tumor-related lesion—Usefulness of the extended observation through use of EMR in combination with Narrow Band Imaging System (NBI)", Digestive Organ Medicine, Japan, 2004, vol. 2, pp. 39-47.

Endo, Takao, et al., "New Viewpoint of the Stomach Cancer Diagnosis and Application to Endoscope", Gastrointestinal Endoscope, Japan, 2004, vol. 16, No. 11, pp. 1659-1667, including an English language abstract.

Muto, Manabu, "Endoscopic Diagnosis and Treatment of Gastrointestinal Tumor—Investigate the Latest Trend<Epidemiology of Gastrointestinal Tumor>Point of Risk Factor and the Early Detection of Oropharynx and Hypopharyngeal Cancer and Esophagus Cancer", Internal Medicine, Japan, 2005, vol. 96, No. 4, pp. 625-629.

Muto, Manabu, "A Risk and Diagnosis of the Hypopharynx and Oropharynx Superficial Cancer", Head and Neck Cancer, Japan, 2005, 31(3), pp. 438-442.

Muto, Manabu, "A Diagnosis and Treatment of the Hypopharynx and Oropharynx Superficial Cancer"—Risk Group and Diagnosis of the Hypopharynx and Oropharynx Superficial Cancer, Otorhinology and Clinical Medicine, Japan, 2005, 51 (Supplement 1), S61-S66.

Sano, Yasushi, et al., "What is Microvessel Diagnostics of Gastrointestinal Cancer, Minute Blood Vessel Diagnostics of Large Intestine Tumor Using Narrow Band Imaging (NB) Colonoscopy", Gastrointestinal Endoscope, Japan, 2005, vol. 17, No. 12, pp. 2129-2138.

Muto, Manabu,et al., "What is Microvessel Diagnostics of Gastrointestinal Cancer-Diagnosis by the Microvessel of Hypopharynx Epibiosis-related Cancer", Gastrointestinal Endoscope, Japan, 2005, vol. 17, No. 12, pp. 2061-2068.

(56) References Cited

OTHER PUBLICATIONS

Next-Generation Columbus: Advanced Digital Technology (10) Capsuled Endoscope. Interview with Mr. Shinichiro Murakami from Olympus, from Special Light Observation to a Capsule Type Endoscope, The World of an Endoscope Accomplishing Evolution Monthly Magazine of For n: Future of Radio Network, Japan, 2006, vol. 11, pp. 76-79.
Nakamura, Kazunari, "High Optics Technique in the Endoscope System", Optics, Japan, 2006, vol. 35, No. 10, pp. 500-507, including an English language abstract.
Katada, Chikatoshi, et al., "The New Medical Treatment System Which Endoscope Observation of the Head and Neck Region with the Extended Gastrointestinal Endoscope and Narrow Band Imaging (NBI) System Bring", Kitazato Medicine, Japan, 2006, 36, pp. 97-101.
Takebashi, Sakae, "Principles and Characteristics of Narrow Band Imaging (NBI)", Specialized Medicine, Japan, 35, pp. 1-7.
Horinouchi, Hiyouki, et al., "Bronchoscope Diagnosis Using Narrow Band Imaging (NBI)", Specialized Medicine, Japan, 35, pp. 12-17.
Watanabe, Akihito, "Early Cancer Diagnosis by NBI Electronic Scope in Otolaryngology Field", Specialized Medicine, Japan, 35, pp. 8-11.
English abstract only of International Application No. WO 2005/051182 (corresponds to JP 2006-526428).
English abstract only of International Application No. WO 03/021329 (corresponds to JP 2005-502083).
English abstract only of International Application No. WO 01/52723 (corresponds to JP 2003-520635).
Japanese Office Action dated Sep. 24, 2014 in counterpart Japanese Patent Application No. 2013-055463, together with an English language translation.
Japanese Office Action dated Sep. 24, 2014 in counterpart Japanese Patent Application No. 2013-055464, together with an English language translation.
Japanese Office Action dated Sep. 24, 2014 in counterpart Japanese Patent Application No. 2013-055465, together with an English language translation.
Japanese Office Action dated Sep. 24, 2014 in counterpart Japanese Patent Application No. 2013-055466, together with an English language translation.
Japanese Office Action dated Sep. 24, 2014 in counterpart Japanese Patent Application No. 2013-055467, together with an English language translation.
Japanese Office Action dated Jan. 20, 2015 in counterpart Japanese Patent Application No. 2013-055463, together with an English language translation.
Japanese Office Action dated Jan. 27, 2015 in counterpart Japanese Patent Application No. 2013-055463, together with an English language translation.
Japanese Office Action dated Jan. 20, 2015 in counterpart Japanese Patent Application No. 2013-055464, together with an English language translation.
Japanese Office Action dated Jan. 27, 2015 in counterpart Japanese Patent Application No. 2013-055464, together with an English language translation.
Japanese Office Action dated Jan. 20, 2015 in counterpart Japanese Patent Application No. 2013-055465, together with an English language translation.
Japanese Office Action dated Jan. 20, 2015 in counterpart Japanese Patent Application No. 2013-055466, together with an English language translation.
Japanese Office Action dated Jan. 27, 2015 in counterpart Japanese Patent Application No. 2013-055466, together with an English language translation.
Japanese Office Action dated Jan. 20, 2015 in counterpart Japanese Patent Application No. 2013-055467, together with an English language translation.
Japanese Office Action dated Jan. 27, 2015 in counterpart Japanese Patent Application No. 2013-055467, together with an English language translation.
Japanese Office Action dated Jul. 17, 2012 in counterpart Japanese Patent Application No. 2007-335321, together with an English language translation.
Japanese Office Action dated Dec. 18, 2012 in counterpart Japanese Patent Application No. 2007-335321, together with an English language translation.
Japanese Office Action dated Feb. 10, 2015 in counterpart Japanese Patent Application No. 2013-055464, together with an English language translation.
Partial European Search Report dated Apr. 3, 2009 from European Application No. 08 17 1890.0.
Office Action dated Sep. 29, 2011 from U.S. Appl. No. 12/335,833.
Office Action dated Jul. 3, 2012 from U.S. Appl. No. 12/335,833.
Office Action dated Mar. 6, 2013 from U.S. Appl. No. 12/335,833.
Japanese Office Action dated Mar. 31, 2015 from Japanese Patent Application No. 2014-170647, together with an English language translation.
Japanese Office Action dated Jun. 9, 2015 from Japanese Patent Application No. 2014-170647, together with an English language translation.
Written Submission of Published Documents dated Feb. 24, 2014 in Japanese Patent Application No. 2013-55463 with English translation.
Written Submission of Published Documents dated Feb. 24, 2014 in Japanese Patent Application No. 2013-55464 with English translation.
Written Submission of Published Documents dated Feb. 24, 2014 in Japanese Patent Application No. 2013-55465 with English translation.
Written Submission of Published Documents dated Feb. 24, 2014 in Japanese Patent Application No. 2013-55466 with English translation.
Written Submission of Published Documents dated Feb. 24, 2014 in Japanese Patent Application No. 2013-55467 with English translation.
Japanese Office Action dated Jul. 17, 2018 in Japanese Patent Application No. 2017-181767.

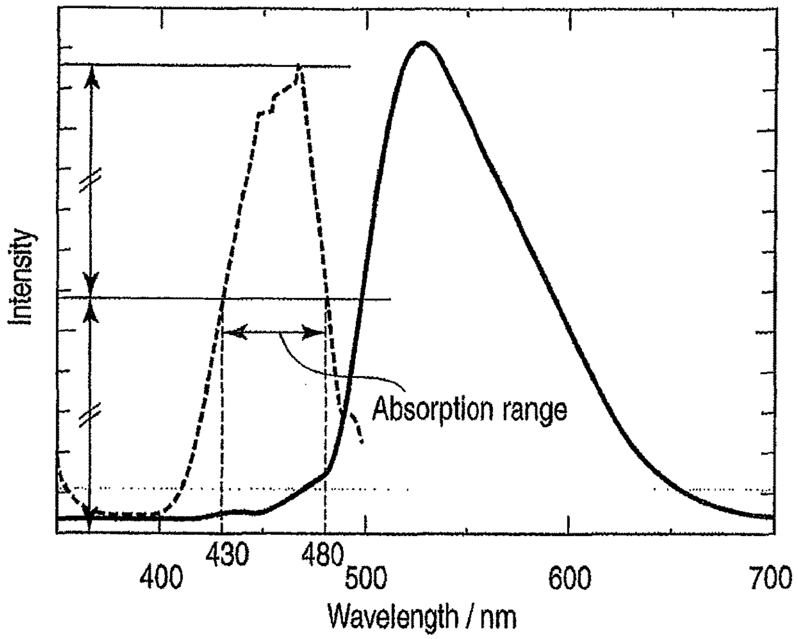
F I G. 2
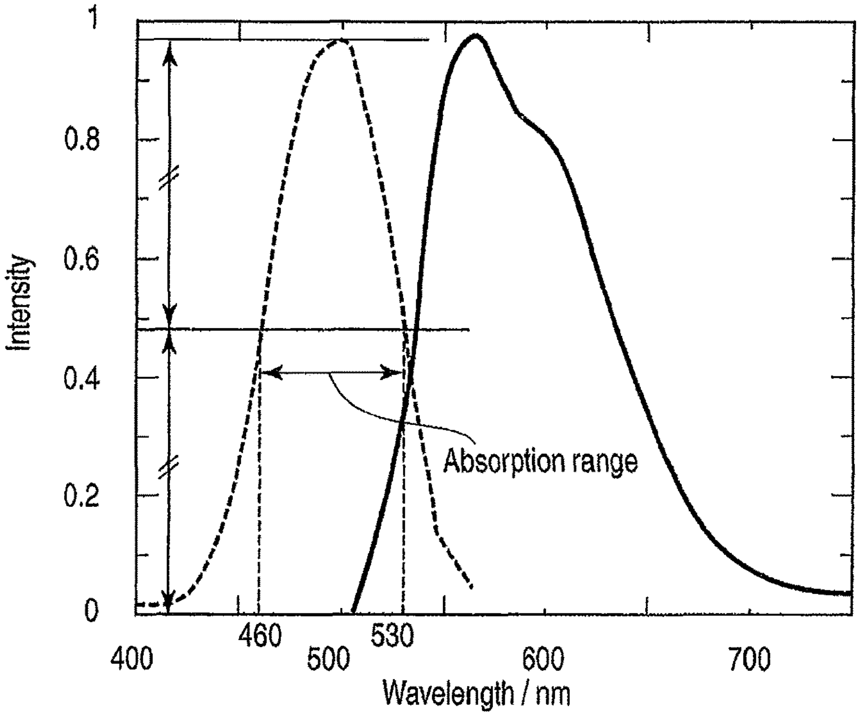
F I G. 3

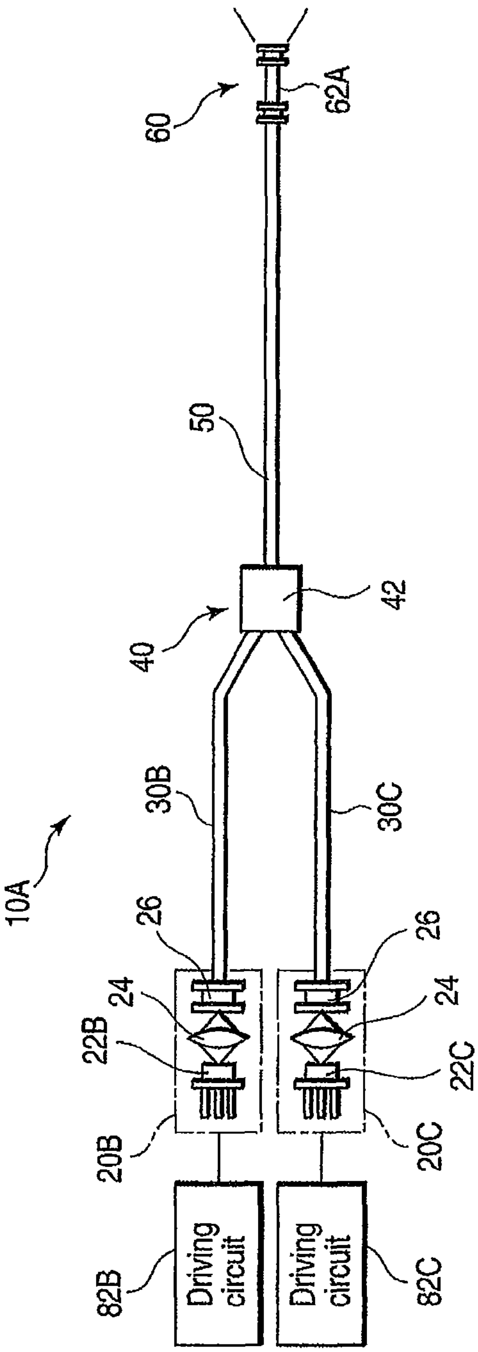
F I G. 4

LIGHT SOURCE DEVICE AND ENDOSCOPE APPARATUS COMPRISING THE SAME

CROSS-REFERENCE TO RELATED APPLICATIONS

This application is a Continuation of U.S. patent application Ser. No. 15/051,104, filed Feb. 23, 2016, which is a Continuation Application of U.S. patent application Ser. No. 14/293,551, filed on Jun. 2, 2014, now U.S. Pat. No. 9,303,830, issued Apr. 5, 2016, which is a continuation of U.S. patent application Ser. No. 13/909,554, filed on Jun. 4, 2013, now U.S. Pat. No. 8,810,126, issued Aug. 19, 2014, which is a continuation of U.S. patent application Ser. No. 12/335,833, filed on Dec. 16, 2008, now U.S. Pat. No. 8,698,387, issued Apr. 15, 2014, which is based upon and claims the benefit of priority from prior Japanese Patent Application No. 2007-335321, filed on Dec. 26, 2007, the entire contents of each of which are incorporated herein by reference.

BACKGROUND OF THE INVENTION

1. Field of the Invention

The present invention relates to a light source device.

2. Description of the Related Art

Currently, an endoscope apparatus performs, in addition to ordinary observation using white light, a narrow band imaging, that is, an observation scheme in which the visibility of a lesion part or the like is improved using light having a specific wavelength. The endoscope apparatus having such a function is, more specifically, configured to switch between white light for ordinary observation and light having a specific wavelength for narrow band imaging, which is referred as special light hereinafter, projecting selected light from the end portion of an endoscope.

Jpn. Pat. Appln. KOKAI Publication No. 2006-026128 discloses a light source device for such an endoscope apparatus. In this light source device, a unit including a light-deflecting element is slid so that the light-deflecting element is arranged on an optical path as required, which performs switching between the white light for ordinary observation and the special light, in other words, switching the projection light colors.

Since switching between the white light and special light is performed by sliding the unit, the light source device described above requires a mechanism for sliding the unit. This results in a bulky, complicated device.

BRIEF SUMMARY OF THE INVENTION

The present invention has been made in view of this situation, and as has its object to provide a compact light source device that can switch the projection light colors.

A light source device according to the present invention includes a first semiconductor light source, a second semiconductor light source, and a wavelength converter. The first semiconductor light source emits light in a first wavelength range. The second semiconductor light source emits light in a second wavelength range different from the first wavelength range. The wavelength converter absorbs the light in the first wavelength range to emit light in a third wavelength range different from either of the first wavelength range and the second wavelength range, and transmits the light in the second wavelength range substantially entirely.

According to the present invention, a compact light source device that can switch the projection light colors is provided.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 shows the spectrum characteristics of YAG:Ce;

FIG. 3 shows the spectrum characteristics of Ce-activated $Ca_3Sc_2Si_3O_{12}$;

FIG. 4 shows a light source device according to the second embodiment of the present invention;

DETAILED DESCRIPTION OF THE INVENTION

The embodiments of the present invention will be described with reference to the accompanying drawing.

<First Embodiment>

Figure 1:
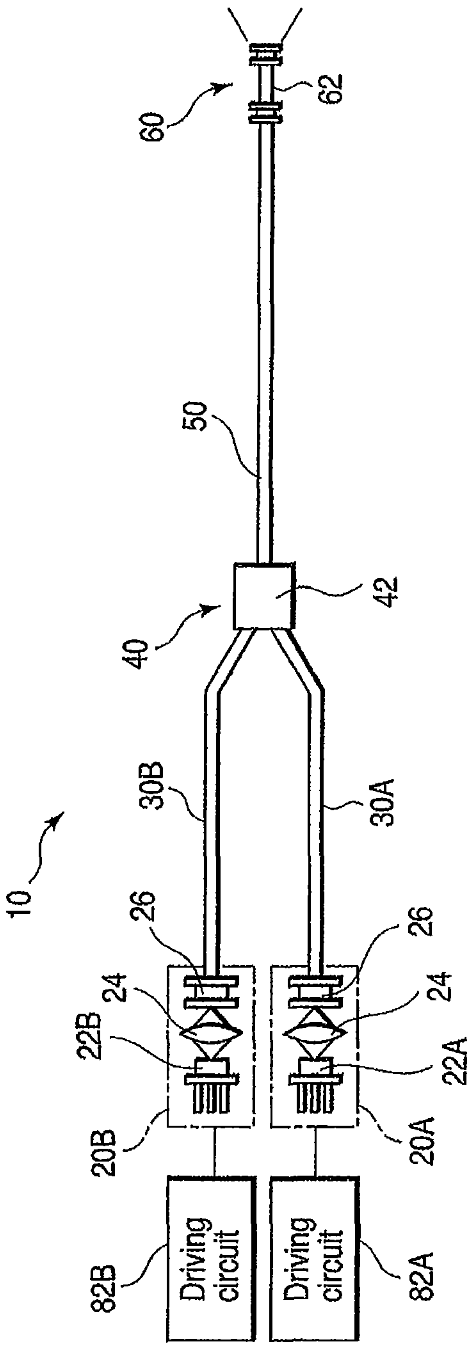
FIG. 1 shows a light source device according to the first embodiment of the present invention.

FIG. 1 shows a light source device according to the first embodiment of the present invention. As shown in FIG. 1, a light source device 10 has a first light source 20A, a second light source 20B, an optical fiber 30A to guide light projected from the first light source 20A, an optical fiber 30B to guide light projected from the second light source 20B, a photocoupler 40 connected to the optical fibers 30A and 30B, an optical fiber 50 to guide light output from the photocoupler 40, and a wavelength converter 60 to emit illumination light corresponding to the light guided by the optical fiber 50.

The first light source 20A has a first semiconductor laser 22A, a lens 24 to converge divergent light emitted from the first semiconductor laser 22A, and a connecting element 26 to optically connect the light converged by the lens 24 to the optical fiber 30A. Similarly, the second light source 20B has a second semiconductor laser 22B, a lens 24 to converge divergent light emitted from the second semiconductor laser 22B, and a connecting element 26 to optically connect the light converged by the lens 24 to the optical fiber 30B.

The light source device 10 further has a driving circuit 82A to switch light on and light off of the first semiconductor laser 22A, that is, turns on and off the first semiconductor laser 22A independently, and a driving circuit 82B to switch light on and light off of the second semiconductor laser 22B, that is, turns on and off the second semiconductor laser 22B independently.

The photocoupler 40 comprises a two-input, one-output optical fiber coupler 42, which has two incident ends and one exit end. One incident end of the optical fiber coupler 42 is optically connected to the first light source 20A through the optical fiber 30A. The other incident end of the optical fiber coupler 42 is optically connected to the second light source 20B through the optical fiber 30B. The exit end of the optical fiber coupler 42 is optically connected to the wavelength converter 60 through the optical fiber 50.

The photocoupler referred to here is what serves to optically connect light from incident ends to at least one exit end, and its connection structure is not limited at all. For example, the photocoupler may be one fabricated by removing the claddings of two or more optical fibers respectively partially, and then heating and pressing the optical fibers in contact with each other, thus connecting the cores of the optical fibers. Alternatively, the photocoupler may be one fabricated by bringing the ends of parallel optical fibers into contact with the end of another optical fiber that opposes them, and heating the resultant structure, thus connecting the optical fibers to the opposing optical fiber. In these two examples, the connecting portion may be called part of the photocoupler, or the connecting portion itself may be called the photocoupler. In either case, the incident optical fibers to guide incident light to the connecting portion can be called incident optical fibers connected to the incident end of the photocoupler, and the exit optical fiber to guide light emerging from the connecting portion to the exit end can be called an exit optical fiber connected to the exit end of the photocoupler.

The first semiconductor laser 22A emits blue laser light having a wavelength of 460 nm, and the second semiconductor laser 22B emits violet laser light having a wavelength of 415 nm. The wavelength converter 60 comprises a phosphor unit 62 including a phosphor of Ce (cerium)-activated YAG (yttrium-aluminum-garnet) (to be referred to as YAG:Ce hereinafter). FIG. 2 shows the spectrum characteristics of YAG:Ce. In FIG. 2, the broken line represents the absorption spectrum of YAG:Ce, and the solid line represents its emission spectrum. As shown in FIG. 2, the absorption spectrum of YAG:Ce has its peak near 460 nm. The absorption range of the absorption spectrum is defined as a wavelength range where the absorption strength of the absorption spectrum of a given phosphor is half or more the peak value. The absorption range of the absorption spectrum of YAG:Ce is approximately 430 nm to 480 nm. The phosphor unit 62 absorbs 460-nm wavelength blue light emitted from the first semiconductor laser 22A to emit light having a wavelength of approximately 530 nm, but almost entirely transmits the 415-nm wavelength violet light emitted from the second semiconductor laser 22B.

The operation of the light source device according to this embodiment will be described.

First, operation that takes place when the first semiconductor laser 22A is turned on will be described. When the first semiconductor laser 22A is turned on, it emits 460-nm wavelength blue laser light. A beam of the laser light emitted from the first semiconductor laser 22A is converged by the lens 24 and then enters the optical fiber 30A. The laser light entering the optical fiber 30A is guided through the optical fiber 30A, travels through the optical fiber coupler 42, is guided through the optical fiber 50, and enters the phosphor unit 62. As is understood from FIG. 2, the 460-nm wavelength blue laser light is light within the absorption range of YAG:Ce. Thus, part of the blue laser light entering the phosphor unit 62 is wavelength-converted by YAG:Ce in the phosphor unit 62 into broad-spectrum yellow light having a peak near a wavelength of 530 nm. The wavelength-converted yellow light is projected from the exit end of the phosphor unit 62. Part of the remaining blue laser light entering the phosphor unit 62 passes through the phosphor unit 62 without wavelength conversion and is projected from the exit end of the phosphor unit 62. Consequently, the yellow light wavelength-converted by the phosphor unit 62 and the blue light emitted from the semiconductor laser 22A are projected from the exit end of the phosphor unit 62. In this embodiment, the yellow light and blue light are adjusted to form white light when mixed. As a result, white light is projected from the exit end of the phosphor unit 62. More specifically, when the first semiconductor laser 22A is turned on, white light as observation light for ordinary observation is projected from the exit end of the phosphor unit 62.

Subsequently, operation that takes place when the second semiconductor laser 22B is turned on will be described. When the second semiconductor laser 22B is turned on, it emits 415-nm wavelength violet laser light. A beam of the laser light emitted from the second semiconductor laser 22B is converged by the lens 24 and then enters the optical fiber 30B. The laser light entering the optical fiber 30B is guided through the optical fiber 30B, travels through the optical fiber coupler 42, is guided through the optical fiber 50, and enters the phosphor unit 62. As is understood from FIG. 2, the 415-nm wavelength violet laser light is not included in the absorption range of YAG:Ce, and is accordingly hardly absorbed by YAG:Ce of the phosphor unit 62. Thus, the violet laser light entering the phosphor unit 62 passes through it almost entirely and is projected from its exit end. More specifically, when the second semiconductor laser 22B is turned on, 415-nm wavelength violet light as observation light for special observation is projected from the exit end of the phosphor unit 62.

In this manner, the light projected from the phosphor unit 62 when only the first semiconductor laser 22A is turned on and the light projected from the phosphor unit 62 when only the second semiconductor laser 22B is turned on have different colors.

In the light source device 10 of this embodiment, when one of the first and second semiconductor lasers 22A and 22B is selectively turned on, the white light as the observation light and the 415-nm wavelength violet light as the special light are switched without using any movable mechanism such as a slide guide unit, and the selected light is projected from the same exit end of the phosphor unit 62.

By combining the two semiconductor lasers 22A and 22B, photocoupler 40, and wavelength converter 60, a light source device that can perform switching between white light and violet light easily is fabricated. Since this light source device has a simple structure with no movable mechanism, it is suitable for downsizing.

In this embodiment, the 415-nm wavelength violet light is selected because it is largely absorbed by hemoglobin in the blood and thus facilitates observation of a blood vessel.

However, the present invention is not limited to the light having this wavelength, but any light having a wavelength matching the observation object may be selected. More specifically, for YAG:Ce, light having a wavelength of 430 nm or less or light having a wavelength of 480 nm or more may be employed.

The phosphor is not limited to YAG:Ce but any other appropriate phosphor such as a phosphor of Ce-activated $Ca_3Sc_2Si_3O_{12}$ may be employed. FIG. 3 shows the spectrum characteristics of Ce-activated $Ca_3Sc_2Si_3O_{12}$. In FIG. 3, the broken line represents the absorption spectrum, and its solid line represents the emission spectrum. As shown in FIG. 3, the absorption range of Ce-activated $Ca_3Sc_2Si_3O_{12}$ is approximately 460 nm to 530 nm. Hence, when using this phosphor, the wavelength of the excitation light of the first semiconductor laser 22A may be set to, e.g., approximately 500 nm, so that the excitation light is wavelength-converted more efficiently to obtain bright illumination light.

<Second Embodiment>

A light source device according to the second embodiment will be described with reference to FIGS. 4 to 9. In the second embodiment, a description on portions that are common with their equivalents in the first embodiment will not be repeated, and portions that are different from their equivalents will mainly be made.

FIG. 4 shows a light source device according to the second embodiment. As shown in FIG. 4, when compared to the light source device 10 of the first embodiment, a light source device 10A according to the second embodiment has a third light source 20C in place of the first light source 20A, an optical fiber 30C in place of the optical fiber 30A, and a phosphor unit 62A in place of the phosphor unit 62. The third light source 20C has a third semiconductor laser 22C, a lens 24 to converge divergent light emitted from the third semiconductor laser 22C, and a connecting element 26 to optically connect the light converged by the lens 24 to the optical fiber 30C. The light source device 10A also has, in place of the driving circuit 82A, a driving circuit 82C to switch light on and light off of the third semiconductor laser 22C, that is, turns on and off the third semiconductor laser 22C independently. Except for this, the arrangement of the second embodiment is the same as that of the first embodiment.

Figure 5:
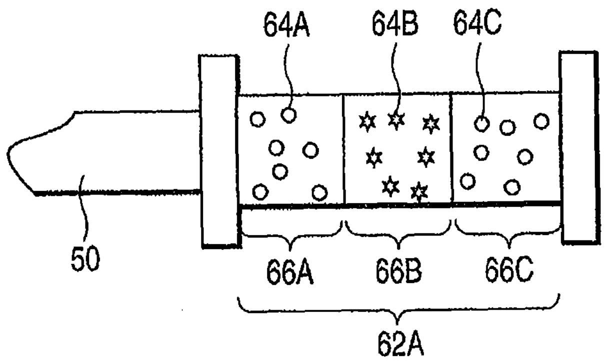
FIG. 5 shows a multi-phosphor unit shown in FIG. 4.
Figure 7:
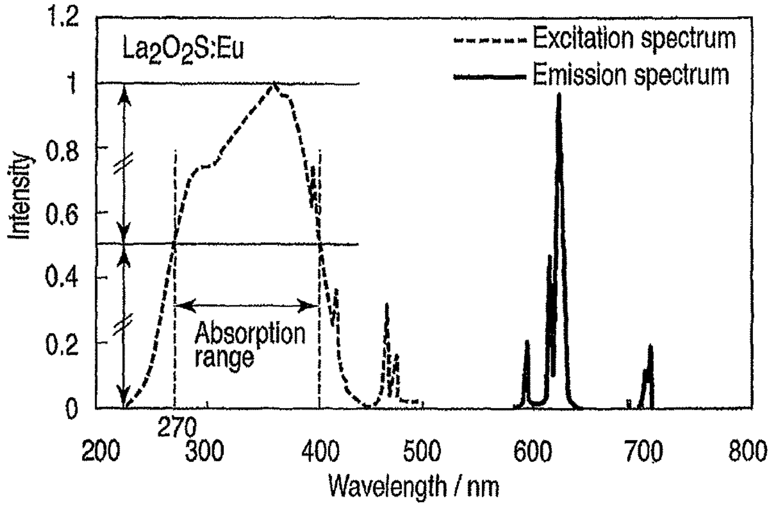
FIG. 7 shows the emission spectrum of Eu-activated $La_2O_2S$.
Figure 8:
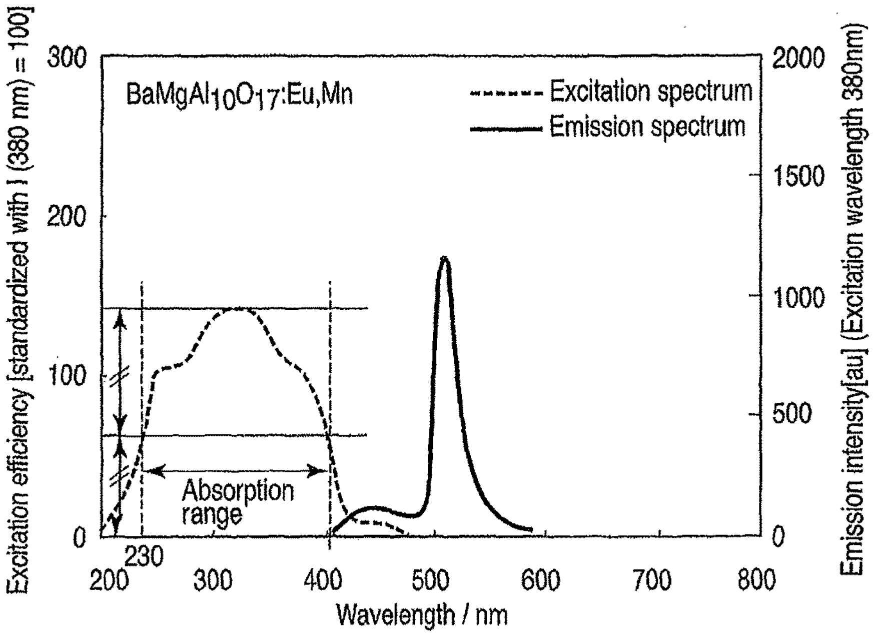
FIG. 8 shows the emission spectrum of Eu, Mn-activated $BaMgAl_{10}O_{17}$.
Figure 9:
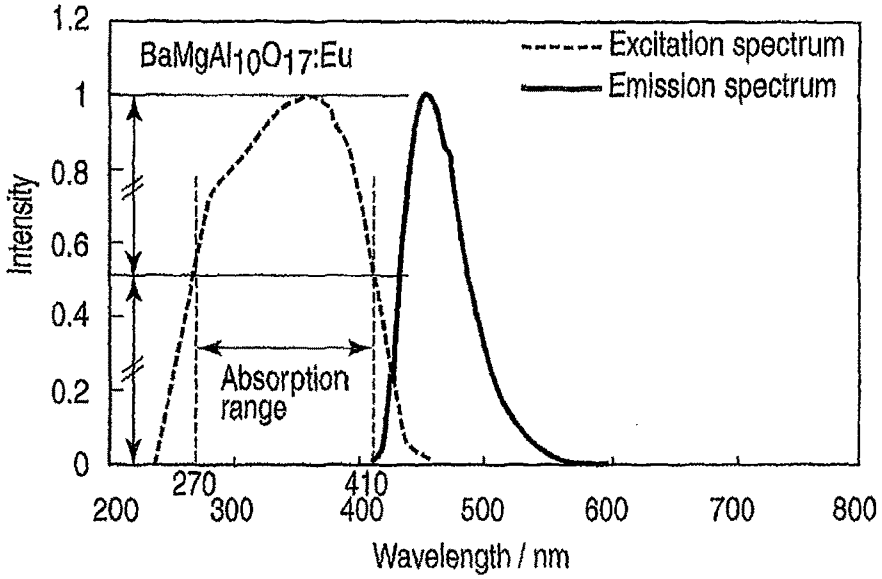
FIG. 9 shows the emission spectrum of Eu-activated $BaMgAl_{10}O_{17}$.

The third semiconductor laser 22C emits near-ultraviolet light having a wavelength of 375 nm. The phosphor unit 62A comprises a multiphosphor unit including different types of phosphors having different compositions. FIG. 5 shows the phosphor unit 62A shown in FIG. 4. As shown in FIG. 5, the phosphor unit 62A comprises the multiphosphor unit formed by stacking a region 66A including R phosphors 64A to emit red light, a region 66B including G phosphors 64B to emit green light, and a region 66C including B phosphors 64C to emit blue light sequentially from the incident end side to the exit light source. As the phosphors 64A, 64B, and 64C, those that respectively emit red light, green light, and blue light upon being excited by 375-nm light as near-ultraviolet light are selected. For example, such phosphors 64A, 64B, and 64C may be Eu-activated $La_2O_2S$ (red), Eu, Mn-activated $BaMgAl_{11}O_{17}$ (green), and Eu-activated $BaMgAl_{10}O_{17}$ (blue), respectively. FIG. 7 shows the emission spectrum of Eu-activated $La_2O_2S$ (red), FIG. 8 shows the emission spectrum of Eu, Mn-activated $BaMgAl_{10}O_{17}$ (green), and FIG. 9 shows the emission spectrum of Eu-activated $BaMgAl_{10}O_{17}$ (blue). As shown in FIGS. 7 to 9, the absorption ranges of these phosphors are 270 nm to 400 nm, 230 nm to 400 nm, and 270 nm to 410 nm, respectively. The absorption range of the multiphosphor unit including these phosphors can be regarded as the overlapping range of the absorption ranges of all the phosphors, which is 270 nm to 400 nm.

The operation of the light source device according to the second embodiment will be described.

When the third semiconductor laser 22C is turned on, it emits 375-nm wavelength near-ultraviolet laser light. A beam of near-ultraviolet laser light emitted from the third semiconductor laser 22C is converged by the lens 24 and enters the optical fiber 30C. The laser light entering the optical fiber 30C is guided through the optical fiber 30C, travels through an optical fiber coupler 42, is guided through an optical fiber 50, and enters the phosphor unit 62A. As shown in FIG. 5, in the phosphor unit 62A, the region 66A including the R phosphors 64A to emit red light, the region 66B including the G phosphors 64B to emit green light, and the region 66C including the B phosphors 64C to emit blue light are arranged sequentially from the incident end side connected to the optical fiber 50. The 375-nm wavelength light emitted from the third semiconductor laser 22C is light within the absorption range of the multiphosphor unit constituting the phosphor unit 62A. Thus, part of the near-ultraviolet light entering the region 66A is wavelength-converted by the R phosphors 64A into red light, and the red light enters the region 66B. Part of the remaining near-ultraviolet light entering the region 66A passes through the region 66A and enters the region 66B. Part of the near-ultraviolet light entering the region 66B is wavelength-converted by the G phosphors 64B into green light, and the green light enters the region 66C. As the G phosphors 64B do not absorb red light, the red light entering the region 66B passes through the region 66B. Therefore, red light, green light, and near-ultraviolet light enter the region 66C including the B phosphors 64C. The near-ultraviolet light entering the region 66C is wavelength-converted by the B phosphors 64C into blue light almost entirely. As the B phosphors 64C do not absorb red light and green light, the red light and green light entering the region 66C pass through the region 66C. As a result, white light as a mixture of the red light, green light, and blue light is projected from the exit end of the phosphor unit 62A.

When the second semiconductor laser 22B is turned on, it emits 415-nm wavelength violet laser light. A beam of light emitted from the second semiconductor laser 22B is converged by a lens 24, enters an optical fiber 30B, is guided through the optical fiber 30B, travels through the optical fiber coupler 42, is guided through the optical fiber 50, and enters the phosphor unit 62A, as described in the first embodiment. The 415-nm wavelength violet light is not light within the absorption range of the multi-phosphor unit. Thus, the violet light entering the phosphor unit 62A is hardly absorbed by the R phosphors 64A, G phosphors 64B, or B phosphors 64C, but passes through the phosphor unit 62A and is projected from the exit end of the phosphor unit 62A.

As a result, the light source device 10A projects white light when the third semiconductor laser 22C is selectively turned on, and 415-nm wavelength violet light when the second semiconductor laser 22B is turned on. As the white light projected from the light source device 10A has components of red light, green light, and blue light, it forms illumination light having higher color rendering properties when compared to the first embodiment. More specifically, according to the second embodiment, a light source device having the same advantages as and better color rendering properties than those of the first embodiment is fabricated.

Figure 6:
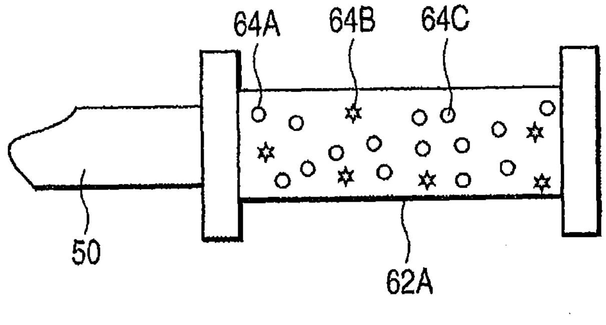
FIG. 6 shows another type of multi-phosphor unit, which can replace the multi-phosphor unit shown in FIG. 5.

In the second embodiment, as shown in FIG. 5, the phosphor unit 62A comprises a multiphosphor unit formed by stacking the region 66A including the R phosphors 64A, the region 66B including the G phosphors 64B, and the region 66C including the B phosphors 64C. Alternatively, as shown in FIG. 6, the phosphor unit 62A may comprise another type of multiphosphor unit in which all of the phosphors 64A, 64B, and 64C are mixed. This simplifies the phosphor unit 62A.

<Third Embodiment>

A light source device according to the third embodiment will be described with reference to FIG. 10. In the third embodiment, a description on portions that are common with their equivalents in the first embodiment will not be repeated, and portions that are different from their equivalents will mainly be described.

Figure 10:
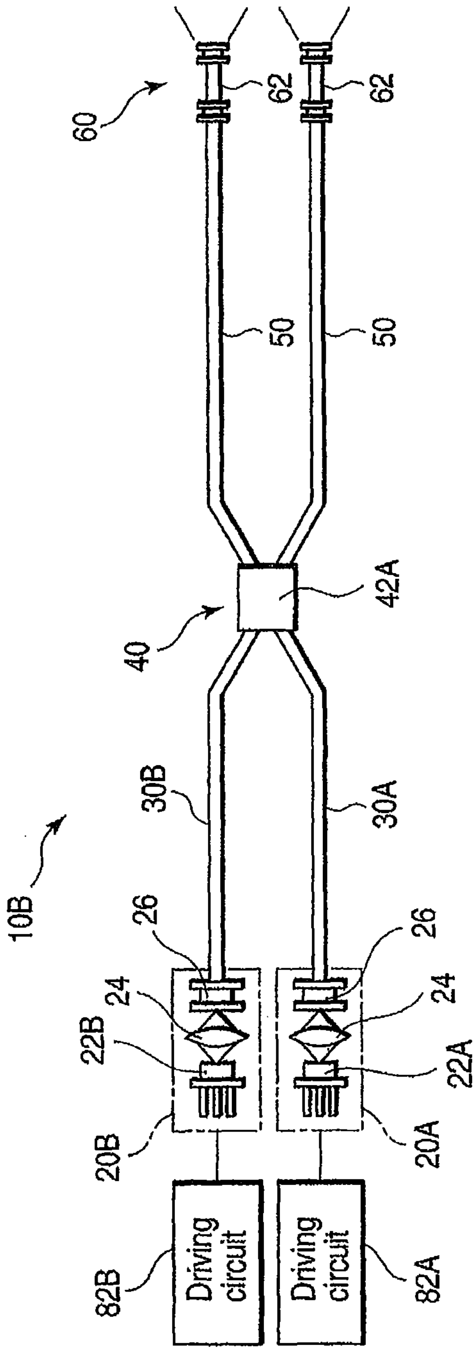
FIG. 10 shows a light source device according to the third embodiment of the present invention.

FIG. 10 shows the light source device according to the third embodiment. As shown in FIG. 10, a light source device 10B according to this embodiment comprises a two-input, two-output optical fiber coupler 42A, which has two incident ends and two exit ends. Two optical fibers 50 and two phosphor units 62 are connected to the two exit ends of the optical fiber coupler 42A. The third embodiment is different from the first embodiment in these respects.

The optical fiber coupler 42A has the two incident ends and two exit ends. The optical fiber coupler 42A distributes light entering one incident end to the two exit ends with substantially equal light intensity proportions, and light entering the other incident end to the two exit ends with substantially equal light intensity proportions. A wavelength converter 60 has the two phosphor units 62. The two phosphor units 62 are optically connected to the two exit ends of the optical fiber coupler 42A, respectively through the two optical fibers 50. The two phosphor units 62 have substantially equal wavelength conversion characteristics.

The 460-nm wavelength blue light emitted from the first semiconductor laser 22A is guided through the optical fiber 30A and enters the optical fiber coupler 42A. The blue light entering the optical fiber coupler 42A is distributed by the optical fiber coupler 42A to the two optical fibers 50 with substantially equal intensities. The blue light distributed to the two optical fibers 50 are respectively guided through the two optical fibers 50 and enter the two phosphor units 62. The blue light entering each phosphor unit 62 forms white light in which blue light and wavelength-converted yellow light are mixed, and the white light is projected from the corresponding phosphor unit 62, as described in the first embodiment.

The 415-nm wavelength violet light emitted from the second semiconductor laser 22B is guided through the optical fiber 30B and enters the optical fiber coupler 42A. The violet light entering the optical fiber coupler 42A is distributed by the optical fiber coupler 42A to the two optical fibers 50 with almost equal intensities. The violet light distributed to the two optical fibers 50 are respectively guided through the two optical fibers 50 and enter the two phosphor units 62. The violet light entering each phosphor unit 62 is directly projected from it, as described in the first embodiment.

According to this embodiment, a light source device that has the advantages of the first embodiment and can illuminate the observation target from two directions is fabricated. For example, as in an endoscope apparatus, when the observation target is very close to the light source, illumination from only one direction may form a shadow, making the observation target difficult to observe. When the exit ends of two phosphor units are arranged to illuminate the observation target from two directions, the observation target will not form a shadow easily. As a result, a light source device that is more suitable for observation is fabricated without making the apparatus bulky.

According to this embodiment, each phosphor unit of the wavelength converter 60 comprises the phosphor unit 62 described in the first embodiment. Alternatively, each phosphor unit may comprise the multiphosphor unit 62A described in the second embodiment. Also, the photocoupler 40 may be changed to an optical fiber coupler having three or more output ends, and the three or more output ends of the optical fiber coupler may be respectively connected to phosphor units and optical fibers corresponding in number to the output ends of the optical photocoupler.

<Fourth Embodiment>

A light source device according to the fourth embodiment will be described. The light source device according to this embodiment basically has an arrangement identical to that of the first embodiment, but is different from the first embodiment in that a wavelength converter 60 comprises a phosphor unit including two types of phosphors having different excitation wavelength characteristics.

A phosphor unit 62 according to this embodiment comprises a phosphor unit including the first phosphor that wavelength-converts blue laser light emitted from a first semiconductor laser 22A but hardly wavelength-converts violet laser light emitted from a second semiconductor laser 22B, and the second phosphor that does not wavelength-convert the blue laser light emitted from the first semiconductor laser 22A but wavelength-converts the violet laser light emitted from the second semiconductor laser 22B.

Figure 11:
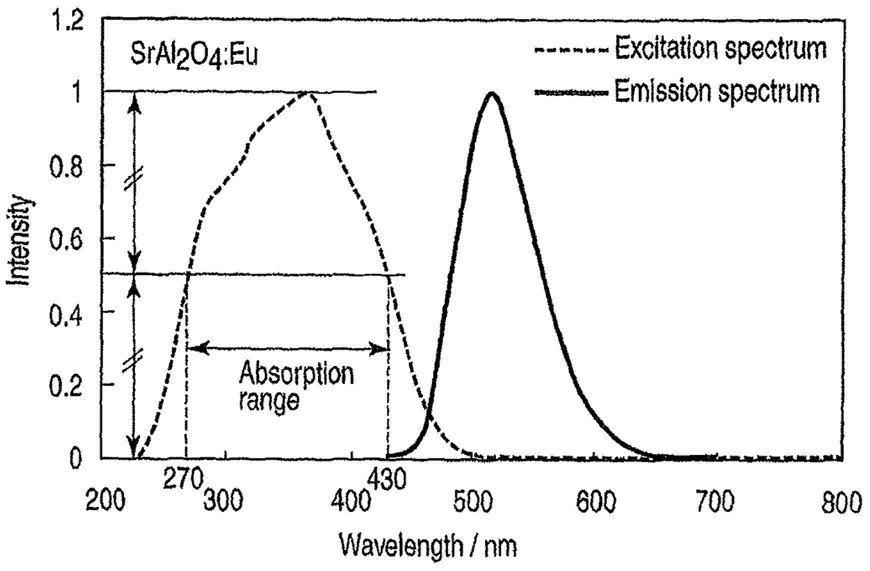
FIG. 11 shows the spectrum characteristics of SrAlO:Eu.

In this embodiment, for example, the first phosphor comprises YAG:Ce, and the second phosphor comprises Eu-activated $SrAl_2O_4$ (to be described as SrAlO:Eu hereinafter). FIG. 2 shows the spectrum characteristics of YAG:Ce, and FIG. 11 shows the spectrum characteristics of SrAlO:Eu. The absorption range of YAG:Ce as the first phosphor is 430 nm to 480 nm, and the absorption range of SrAlO as the second phosphor is 270 nm to 430 nm.

The operation of the fourth embodiment will be described.

Operation that takes place when the first semiconductor laser 22A is turned on will be described first. As described in the first embodiment, the first semiconductor laser 22A emits 460-nm wavelength blue laser light. The laser light emitted from the first semiconductor laser 22A is guided through an optical fiber 30A, travels through an optical fiber coupler 42, is guided through an optical fiber 50, and enters the phosphor unit 62. The phosphor unit 62 includes YAG:Ce having the characteristics shown in FIG. 2 and SrAlO:Eu having the characteristics shown in FIG. 11. The 460-nm wavelength blue light is light within the absorption range of YAG:Ce and outside the absorption range of SrAlO:Eu. Hence, the blue light entering the phosphor unit 62 is efficiently wavelength-converted by YAG:Ce into yellow light having a wavelength of approximately 530 nm, but is hardly wavelength-converted by SrAlO:Eu. Consequently, white light as a mixture of the blue light and the yellow light, which is wavelength-converted by YAG:Ce, is projected from the exit end of the phosphor unit 62.

Figure 12:
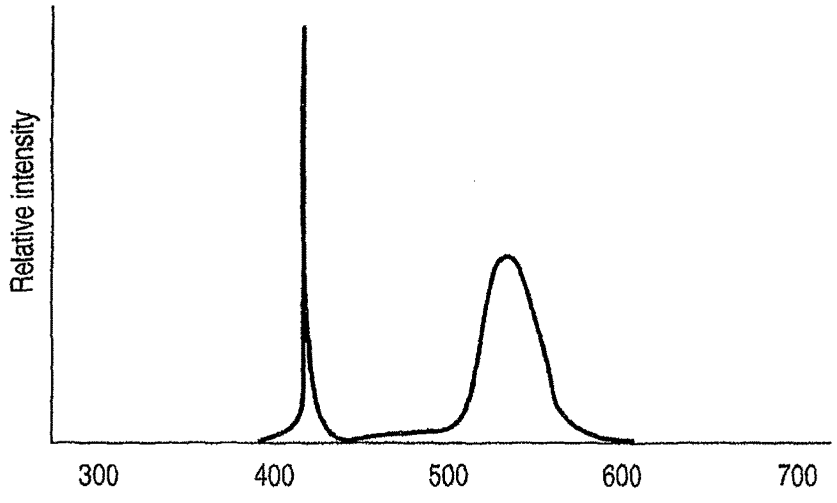
FIG. 12 shows the spectrum of light projected from the phosphor unit of a light source device according to the fourth embodiment of the present invention.

Operation that takes place when the second semiconductor laser 22B is turned on will be described. As described in the first embodiment, the second semiconductor laser 22B emits 415-nm wavelength violet laser light. The laser light emitted from the second semiconductor laser 22B is guided through an optical fiber 30B, travels through the optical fiber coupler 42, is guided through the optical fiber 50, and enters the phosphor unit 62. The 415-nm wavelength violet light is light within the absorption range of SrAlO:Eu and outside the absorption range of YAG:Ce. Hence, the violet light entering the phosphor unit 62 is hardly wavelength-converted by YAG:Ce, but is efficiently wavelength-converted by SrAlO:Eu into green light having a wavelength of approximately 540 nm. Consequently, as shown in FIG. 12, light as a mixture of 415-nm wavelength violet light and 540-nm wavelength green light is projected from the exit end of the phosphor unit 62. The wavelengths of the mixed light generally coincide with the absorption wavelengths of hemoglobin, so that the mixed light is suitable for observation of the blood vessel with a high contrast.

According to this embodiment, a light source device that has the advantages of the first embodiment and is suitable for observation of a blood vessel or the like with a high contrast is fabricated. In this light source device, merely the number of types of phosphors included in the phosphor unit 62 increases and no other major change is needed. Hence, the apparatus does not become bulky.

<Note>

Although the light source comprises a semiconductor laser in all the embodiments described above, the light source is not limited to this, but can comprise another semiconductor light source such as a light-emitting diode. When a light-emitting diode is used, a less expensive light source device is fabricated than a case in which a semiconductor laser is used.

The light source device according to any embodiment descried above is particularly suitably mounted in an endoscope apparatus.

Figure 13:
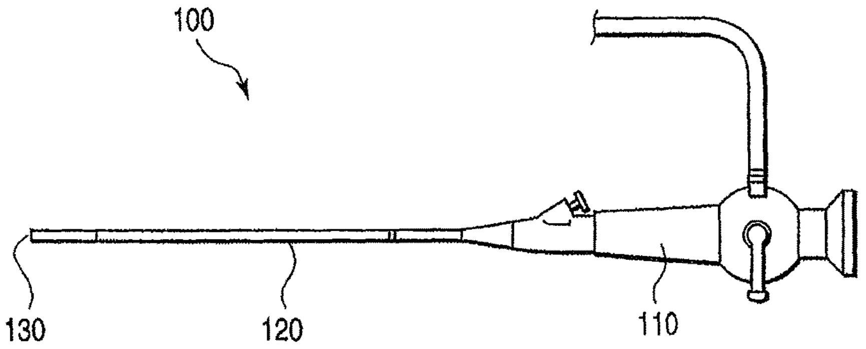
FIG. 13 schematically shows a general endoscope apparatus.

FIG. 13 schematically shows a general endoscope apparatus. As shown in FIG. 13, an endoscope apparatus 100 has a control unit 110, an inserting portion 120 extending from the control unit 110, and an endoscope end portion 130 located at the end of the inserting portion 120. In observation using such an endoscope apparatus 100, the observation target is close to the endoscope end portion 130. If the exit position of ordinary observation light is shifted from that of special light, inconveniences such as color separation occur. In contrast to this, with the light source device according to any one of the embodiments described above, the exit position of ordinary observation light coincides with that of special light, so color separation does not occur. Thus, this light source device is particularly suitably mounted in an endoscope apparatus.

Figure 14:
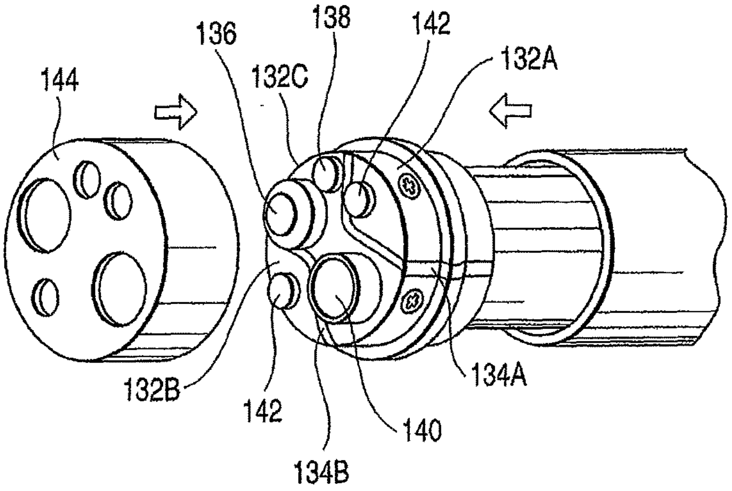
FIG. 14 shows the arrangement of an endoscope end portion shown in FIG. 13.

FIG. 14 shows the arrangement of a general endoscope end portion 130. As shown in FIG. 14, the endoscope end portion 130 has three end metal members 132A, 132B, and 132C, and a cover 144 that covers them. The two end metal members 132A and 132C are connected to each other through a heat-insulating material 134A, and the two end metal members 132B and 132C are connected to each other through a heat-insulating material 134B. The end metal member 132C is provided with a solid-state image sensor 136, an air/water supply nozzle 138, and a suction channel 140. The end metal members 132A and 132B are respectively provided with illumination light guide units 142.

In this manner, the endoscope apparatus generally has the two light guide units 142. When mounting the light source device of any embodiment described above in the endoscope apparatus, two light source devices each having one light-emitting portion may be built into the endoscope apparatus, as shown in FIGS. 1 and 4, or only one light source device having two light-emitting portions may be built into the endoscope apparatus, as shown in FIG. 10.

When mounting the light source device of any embodiment described above in the endoscope apparatus, the wavelength converter 60 may be arranged near the endoscope end portion 130, or light projected from the wavelength converter 60 may be guided to the endoscope end portion 130 through another optical fiber. The former arrangement is preferable for obtaining high-luminance illumination light. The latter arrangement is preferable for suppressing heat generation near the endoscope end portion because a phosphor unit that emits heat is arranged away from the endoscope end portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical device comprising:

a first light source configured to emit a first light having a first wavelength range;

a second light source configured to emit a second light having a second wavelength range, wherein at least a portion of the second wavelength range is different from the first wavelength range; and a first wavelength converter comprising:

wavelength conversion material of a first type, configured to:

wavelength convert a first part of the first light incident on the wavelength conversion material of the first type into a first converted light, wherein the first converted light has a third wavelength range different from the first wavelength range and different from the second wavelength range; and emit a first illumination light comprising the first converted light and a second part of the first light that is transmitted through the first wavelength converter; and wavelength conversion material of a second type, configured to:

wavelength convert a first part of the second light incident on the wavelength conversion material of the second type into a second converted light; and emit a second illumination light comprising the second converted light and a second part of the second light that is transmitted through the first wavelength converter.

2. The optical device according to claim 1, wherein the wavelength conversion material of the first type has a first absorption range defined as a wavelength range in an absorption spectrum of the wavelength conversion material of the first type where absorption strength of the wavelength conversion material of the first type is half or more than half of a peak absorption strength of the wavelength conversion material of the first type, wherein the wavelength conversion material of the second type has a second absorption range defined as a wavelength range in an absorption spectrum of the wavelength conversion material of the second type where absorption strength of the wavelength conversion material of the second type is half or more than half of a peak absorption strength of the wavelength conversion material of the second type, wherein a wavelength at which the first light has a peak intensity is within the first absorption range, and wherein a wavelength at which the second light has a peak intensity is not within the first absorption range and is within the second absorption range.

3. The optical device according to claim 1, wherein the second wavelength range is on a shorter wavelength side of the first wavelength range.

4. The optical device according to claim 1, wherein the wavelength conversion material of the first type is selected to emit the first illumination light for normal observation, and wherein the wavelength conversion material of the second type is selected to emit the second illumination light for special light observation.

5. The optical device according to claim 1, wherein the first light is a blue light having a peak intensity at approximately 460 nm, and wherein the first illumination light is a white light for ordinary observation.

6. The optical device according to claim 1, wherein the wavelength conversion material of the first type is a cerium-activated phosphor, and wherein at least a portion of the first wavelength range is within an absorption wavelength range of the cerium-activated phosphor.

7. The optical device according to claim 1, wherein the wavelength conversion material of the first type is a garnet phosphor, and wherein at least a portion of the first wavelength range is within an absorption wavelength range of the garnet phosphor.

8. The optical device according to claim 1, wherein the wavelength conversion material of the first type is a cerium-activated yttrium-aluminum-garnet, and wherein the second wavelength range is outside of a wavelength range of 430 nm to 480 nm.

9. The optical device according to claim 1, wherein the second light is violet light, and wherein the second illumination light is green light.

10. The optical device according to claim 9, wherein the second converted light has a fourth wavelength range different from the second wavelength range, and wherein both of at least a portion of the second wavelength range and at least a portion of the fourth wavelength range is within an absorption wavelength range of hemoglobin.

11. The optical device according to claim 9, wherein the second light has a peak intensity at approximately 415 nm, and wherein the second illumination light has a peak intensity at approximately 540 nm.

12. The optical device according to claim 1, further comprising:

a control circuit configured to:

control the first light source to emit the first light; and control the second light source to emit the second light.

13. The optical device according to claim 12, wherein the control circuit is configured to:

control the first light source to switch between emitting the first light and not emitting the first light; and control the second light source to switch between emitting the second light and not emitting the second light.

14. The optical device according to claim 13, wherein the control circuit is configured to:

independently control the first light source to switch between emitting the first light and not emitting the first light; and independently control the second light source to switch between emitting the second light and not emitting the second light.

15. The optical device according to claim 1, wherein the first light source is configured to emit the first light as a first laser beam, and wherein the second light source is configured to emit the second light as a second laser beam.

16. The optical device according to claim 1, further comprising:

a first optical fiber configured to guide the first light emitted by the first light source and the second light emitted by the second light source to be incident on the first wavelength converter.

17. The optical device according to claim 16, further comprising:

an optical coupler configured to couple the first light emitted by the first light source and the second light emitted by the second light source, and to cause the first light and the second light that are coupled to enter and be guided by the first optical fiber to be incident on the first wavelength converter.

18. The optical device according to claim 17, further comprising:

a second wavelength converter comprising:

wavelength conversion material of the first type, configured to:

wavelength convert a third part of the first light incident on the wavelength conversion material of the first type of the second wavelength converter into a third converted light, wherein the third converted light has a fifth wavelength range different from the first wavelength range and different from the second wavelength range; and emit a third illumination light comprising the third converted light and a fourth part of the first light that is transmitted through the second wavelength converter; and wavelength conversion material of the second type, configured to:

wavelength convert a third part of the second light incident on the wavelength conversion material of the second type into a fourth converted light; and emit a fourth illumination light comprising the fourth converted light and a fourth part of the second light that is transmitted through the second wavelength converter.

19. An endoscope apparatus comprising the optical device according to claim 1.

20. The endoscope apparatus according to claim 19, further comprising:

an inserting portion configured to be inserted into a subject, wherein the first wavelength converter of the optical device is arranged in the inserting portion.

21. The endoscope apparatus according to claim 20, wherein the first wavelength converter of the optical device is arranged closer to a distal end of the inserting portion than a proximal end of the inserting portion.

22. The endoscope apparatus according to claim 19, wherein the wavelength conversion material of the first type and the wavelength conversion material of the second type are mixed.

23. The endoscope apparatus according to claim 19, wherein the wavelength conversion material of the first type is arranged in a first region, wherein the wavelength conversion material of the second type is arranged in a second region, and wherein the first region and the second region are stacked in a direction such that the first light and the second light are first incident on only one of the first region and the second region.

* * * * *